United States Patent [19]
Ito

[11] 4,298,346
[45] Nov. 3, 1981

[54] VIRUS HEMAGGLUTINATION-INHIBITION REACTION

[75] Inventor: Homu Ito, Nagaokakyo, Japan

[73] Assignee: Takeda Chemical Industries, Ltd., Osaka, Japan

[21] Appl. No.: 85,641

[22] PCT Filed: Jan. 17, 1979

[86] PCT No.: PCT/JP79/00010
§ 371 Date: Oct. 6, 1979
§ 102(e) Date: Jan. 29, 1979

[87] PCT Pub. No.: WO79/00675
PCT Pub. Date: Sep. 20, 1979

[30] Foreign Application Priority Data
Feb. 6, 1978 [JP] Japan .................................. 53-12655
Oct. 11, 1978 [JP] Japan ................................. 53-125434

[51] Int. Cl.$^3$ .............................................. G01N 33/48
[52] U.S. Cl. .................................. 23/230 B; 252/408; 424/8; 424/12; 435/5; 435/7
[58] Field of Search ..................... 23/230 B; 424/12, 8, 424/86, 89, 93; 252/408; 435/5, 7

[56] References Cited
U.S. PATENT DOCUMENTS

| | | | |
|---|---|---|---|
| 3,541,202 | 11/1970 | Meyer, Jr. et al. | 424/12 |
| 3,777,014 | 12/1973 | Zichis | 424/12 |
| 3,828,103 | 8/1974 | Fujita | 424/12 |
| 4,059,491 | 11/1977 | Iwasa et al. | 424/12 |
| 4,140,754 | 2/1979 | Iwasa | 424/12 |
| 4,195,074 | 3/1980 | Safford, Jr. | 424/12 |

FOREIGN PATENT DOCUMENTS

| | | | |
|---|---|---|---|
| 2429231 | 1/1975 | Fed. Rep. of Germany | 424/12 |
| 52-154518 | 12/1977 | Japan | 252/408 |
| 646992 | 2/1979 | U.S.S.R. | 424/12 |

OTHER PUBLICATIONS

C. A., vol. 88, p. 386, 134783h, (1978).
Auletta, A. E., et al., Appl. Microbio., vol. 16, No. 5, pp. 691–694, (1968).
Clarke, D. H., et al., Amer. J. Trop. Med. Hyg., vol. 7, pp. 561–573, (1958).
Sever, J. L., et al., Pediatrics, vol. 40, No. 5, pp. 789–797, (1967).
Schmidt, N. J., et al., Appl. Microbiol., vol. 22, No. 3, pp. 469–470, (1971).
Mann, J. J., et al., J. Immunology, vol. 98, No. 6, pp. 1136–1142, (1967).
Gupta, J. D., et al., Appl. Microbiol., vol. 20, No. 5, pp. 843–844, (1970).

Primary Examiner—Teddy S. Gron
Attorney, Agent, or Firm—Wenderoth, Lind & Ponack

[57] ABSTRACT

The nonspecific hemagglutination inhibitors and natural hemagglutinins in a test serum for a virus hemagglutination-inhibition reaction can be removed at one stroke in a convenient procedure by pretreating the test serum with a composition containing both fixed avian erythrocytes and kaolin particles.

3 Claims, No Drawings

VIRUS HEMAGGLUTINATION-INHIBITION REACTION

DESCRIPTION

TECHNICAL FIELD

The present invention relates to virus hemagglutination-inhibition reactions useful as serological diagnosis.

BACKGROUND ART

The hemagglutination-inhibition (hereinafter briefly referred to as HI) reactions of viruses is more sensitive and more expedient to perform than neutralization and complement-fixation tests, and have been employed as a useful means of serological diagnosis. The test sera of human beings and other animals that are subjected to viral HI reactions contain nonspecific hemagglutination inhibitors and natural hemagglutinins which must be removed or inactivated before the HI reactions are carried out. The common procedure heretofore taken for this purpose is a two-step procedure which comprises adding kaolin particles to the test serum, incubating the mixture to adsorb and remove the nonspecific hemagglutination inhibitors, centrifuging the same and incubating the supernatant with erythrocytes to cause neutral agglutinins to be adsorbed on the erythrocytes. However, this two-step procedure is not sufficiently expedient in that, for example, it not only requires a plurality of incubating steps and an intermediate centrifugation step but involves the use of dissimilar buffers for carrying out those two steps.

In the face of the above technical obstacles, intensive research was conducted by the present inventor for the resolution of the above-mentioned disadvantages. The research led to the novel and unexpected finding that both nonspecific hemagglutination inhibitors and natural hemagglutinins can be removed almost completely in a very convenient procedure by pretreating the test serum with a composition containing both fixed avian erythrocytes and kaolin particles. Further research based upon the said finding resulted in the completion of the present invention.

DISCLOSURE OF INVENTION

The present invention provides a composition for pretreatment of test sera for viral HI reactions containing both fixed avian erythrocytes and kaolin particles. Another object of this invention is to provide an improved method for viral HI reactions, which comprises pretreating the test sera with the said composition and employing fixed avian erythrocytes as the erythrocytes to be agglutinated. Other objects will be made clear from the description and claims presented hereinafter.

The pretreating composition of this invention is applicable to test serum for any viral HI reaction. As example of the virus to which this invention is applicable there may be mentioned togaviruses (rubella virus; arboviruses such as Japanese B encephalitis virus, yellow fever virus, Dengue virus, etc.), orthomyxoviruses (influenza A virus, influenza B virus, etc.), paramyxoviruses [Sendai virus (HVJ), Newcastle disease virus, mumps virus, etc.] and so on.

The pretreating composition of the present invention is a novel composition which contains both fixed avian erythrocytes and kaolin particles.

In accordance with this invention, the erythrocytes of any avian species which will be agglutinated by the virus-specific hemagglutinating antigen (hereinafter briefly referred to as HA antigen) can be employed. As typical examples of such avian species there may be mentioned chicken, geese, duck, turkey, quail and so on. Particularly advantageous are the erythrocytes of unfed newly-hatched chicks not older than 48 hours old. The fixation of such erythrocytes may be carried out with a fixing agent commonly used for similar purposes, e.g. formalin or glutaraldehyde. When formalin, for instance, is employed, erythrocytes may be successfully treated with formalin containing about 1 to 20% (hereinafter percentages are weight/volume unless otherwise specified) of formaldehyde, the salt concentration of which is isotonic to the erythrocytes, at a temperature between about 2° C. and 40° C., preferably at about 37° C. The erythrocytes thus fixed are washed with water, prior to use, to remove the adherent fixing agent, salts, etc.

If desired, prior to the fixing treatment, the erythrocytes may be colored cherry-red with carbon monoxide gas.

The kaolin particles may be of any mesh size as long as they are able to adsorb and remove nonspecific hemagglutination inhibitors. Generally preferred are kaolin particles within the size range of about 100 to 325 Tyler mesh.

The pretreatment composition of this invention may be either in a form of a suspension in an aqueous medium or in a lyophilized form. The aqueous medium for said suspension is based on water, which may for example be distilled water or a buffer suitable for the object virus. Generally preferable is a medium of pH about 6.0 to about 9.0. As typical examples of buffers suited for the above-mentioned togaviruses, orthomyxoviruses and paramyxoviruses, there may be mentioned phosphate buffer solutions within the pH range of about 6.0 to 7.4 [for example -PBS (cf. Examples hereinafter), etc.] and borate buffers within the pH range of about 7.0 to 9.0 [e.g. BS 9.0 (cf. Examples hereinafter), etc.].

The suspension prepared with such a buffer may be directly applied to HI test sera for the particular viral species. On the other hand, the suspension in distilled water can be applied to HI test sera for a variety of viruses, on extemporaneous processing thereof into a buffered system suitable for the particular virus.

The preferred erythrocyte amount of such an aqueous suspension at the time of use is in the range from about 0.2 to about 20%, especially about 2% (volume/volume), while the preferred amount of kaolin particles is about 5 to about 20%, especially about 14%.

The pretreating suspension thus obtained is stable (over at least a year at about 4° C.) and, in use, it removes both nonspecific hemagglutination inhibitors and natural hemagglutinins from test sera in one step on mere admixture with the test sera and leaving the mixture standing at room temperature for, e.g. about 30 minutes (with a few shakings as desired). The test serum thus treated can be centrifuged and immediately subjected to an HI reaction.

The pretreating composition in a lyophilized form may be prepared by lyophilizing the above-mentioned aqueous suspension. It is most desirable to freeze-dry a suspension of fixed avian erythrocytes and kaolin particles in distilled water. This freeze-drying operation is preferably carried out in two steps, i.e. rapid preliminary freezing and subsequent vacuum freeze-drying. The rapid preliminary freezing is accomplished by, for example, immersing a vial of the suspension in a mixture of dry-ice with either methanol or acetone. The vial is then placed in the chamber rack of a freeze-dryer previously cooled to −40° C. to −50° C. and freeze-dried in vacuo for 24 to 48 hours. The vial is then sealed in vacuo or after filling with nitrogen gas. While the scatter of erythrocytes in this process is almost negligible, it may be prevented more positively, if desired, by freeze-drying the suspension in the presence of about 1 to 30% of dextrose.

The lyophilized composition thus obtained is highly stable (e.g. stable over at least 2 years at 4° C.) and, on mere re-suspension in a buffer suitable for any of said large variety of viruses, can be applied to test serum for a viral HI reaction in the same manner as the aqueous suspension mentioned above.

By this pretreatment with the composition of the present invention, both nonspecific hemagglutination inhibitors and natural hemagglutinins in a test serum can be removed at one stroke but the activity of a virus-specific HI antibody occurring in the same serum is not adversely affected.

Thus-pretreated test serum may be subjected to an HI reaction in the manner known per se. Thus, the test serum is mixed with a virus-specific HA antigen and then with the fixed erythrocytes of the same kind as that employed for the pretreating composition to assess the occurrence or non-occurrence of hemagglutination. In performing this HI test, use may be made of any technique applicable for virus HI tests, such as the microtiter method. For example, such an HI test may be performed as follows. Thus, 0.025 ml. of the pretreated test serum is serially diluted in two-fold steps on a microplate and 0.025 ml. of a virus-specific hemagglutinating antigen with 4 hemagglutination units is added. The system is allowed to stand at room temperature for 60 minutes, after which time 0.050 ml. of a 0.25% suspension of fixed erythrocytes is mixed with the above system. The system is allowed to stand at a temperature suitable for the object virus, e.g. at 37° C. or room temperature for an arbovirus, at 4° C. or room temperature for an orthomyxovirus, paramyxovirus or rubella virus, for 60 minutes, and the occurrence or non-occurrence of hemagglutination is investigated. The virus HI antibody titer is the reciprocal of the highest dilution factor of the test serum with completely inhibited hemagglutination. By this procedure, the virus HI antibody titer of the test serum can be determined with accuracy and high sensitivity.

In case of arbovirus HI reaction, the present invention attains another advantage by employing fixed avian erythrocytes as the erythrocytes to be agglutinated. As a characteristic feature of the HI reactions of arboviruses, their dependence on the pH of the reaction diluent is high. Moreover, the optimal pH range varies widely with different viral species and strains. Another important aspect of what has been mentioned so far in connection with pH for HI reactions of arboviruses is that whereas arbovirus-specific HA antigens are relatively stable on the alkaline side (pH approx. 9.0), the optimal pH for the reaction of erythrocytes with the specific HA antigens lies on the acidic side (pH 6.2 to 6.8). To make a compromise between these two requirements, it has been necessary heretofore to perform the following preliminary test:

The dilution of the arbovirus-specific HA antigen and the test serum for the titration of the antibody as well as the admixing of the two is carried out using a borate-buffered saline of pH 9.0 supplemented with bovine serum albumin of 0.4% (hereinafter briefly referred to as BBS). Prior to the HI test, it is necessary to determine the optimal pH for the HA reaction. For this purpose, erythrocytes are suspended in a phosphate buffered saline called "virus adjusting diluent (VAD)" on the acidic side and the suspension added to the arbovirus-specific HA antigen diluted with BBS of pH 9.0. The VAD with a pH making for the highest HA activity is thus determined. The erythrocytes are suspended in this particular VAD, the number of specific antigen units for the HI test is determined and the VAD of this pH is employed also in the HI test which is now performed. A VAD series is prepared in such a manner that they will give final pHs between 5.8 and 7.0 upon admixture with BBS, at intervals of pH 0.2.

The conventional HI reaction with an arbovirus requires such a time-consuming preliminary test. Moreover, since the ionic strength of VAD is high, the possibility of hemolysis is high on the acidic side and for this latter reason, the conventional procedure had the disadvantage that the erythrocyte suspension had to be prepared only immediately before admixing with the specific HA antigen.

The present inventor has unexpectedly found that when an HI reaction of an arbovirus is conducted using fixed avian erythrocytes, the above-mentioned high pH dependence was eliminated so that the HI reaction can be conducted in the broad pH ranges of pH 6.6 to 12.0. Thus, the pretreated test serum, the arbovirus-specific HA antigen and the fixed avian erythrocytes are all diluted with a buffer solution in the pH range of 6.6 to 12.0, preferably of 6.9 to 9.0, especially of 6.8 to 7.2. It is preferable that this buffer solution contains NaCl in a concentration of 0.35 to 0.85%. As the typical examples of such buffers, there may be mentioned phosphate buffered saline [e.g. -PBS (c.f. Examples hereinafter)], HEPES (N-2-hydroxyethylpiperazine-N'-2'-ethansulfonic acid)-buffered saline and BBS. It is advantageous that this diluent further contains albumin, which preferably is serum albumin, especially bovine serum albumin, in a concentration of from about 0.1 to about 1% (volume/volume), as well as gelatin in a concentration of from about 0.00025 to about 0.05%, especially about 0.005%.

According to this invention, the arbovirus HI reactions can be conducted using one common diluent for test sera, HA antigens and fixed avian erythrocytes while omitting the preliminary test required in the conventional techniques.

Best Mode for Carrying Out the Invention

EXAMPLE 1

(1) Washing and sterilization of kaolin 453 g. of kaolin (Acid washed kaolin; Fischer Scientific Company (U.S.A.), particle size 200 to 250 Tyler mesh) was washed once with BS 9.0 *[1]) and 5 times with distilled water, made up as a 14% suspension in distilled water and finally heat-sterilized at 10 pounds for 10 minutes.

---

*[1])BS 9.0 stands for Borate-Saline, pH 9.0, the composition of which is as follows.

| | |
|---|---|
| 0.5M $H_3BO_6$ | 100 ml. |
| 1.5M NaCl | 80 ml. |
| 1.0 M NaOH | 24 ml. |
| Distilled water to make | 1,000 ml. |

(2) Preparation of fixed one-day-old chick erythrocytes

Using a 5 ml.-syringe filled with 0.3 ml. of ACD*[2] each unfed one-day-old chick was bled by cardiac puncture with the needle being inserted from a position superior to the sternum toward the abdomen. The chick bloods were pooled in a 1000 ml. bottle and, following addition of about 2 volumes of DGV*[3], filtered through 4 layers of gauze. The filtrate was centrifuged at 1500 r.p.m. for 5 minutes, the supernatant was discarded and the sediment was washed 3 times with about 20 times its volume of DGC. The final centrifugation was performed at 1500 r.p.m. for 10 minutes and, based on the packed-cell sediment, 9 times its volume of -PBS*[4] was added to the sediment to prepare a 10% suspension of erythrocytes. Carbon monoxide gas was bubbled into the above 10% suspension (60 to 120 bubbles/minute) for 5 minutes and the resultant cherry-red erythrocytes were harvested by centrifugation at 1,500 r.p.m. for 5 minutes and resuspended in -PBS to prepare a 10% suspension.

---

*[2]ACD stands for Acid-Citrate-Dextrose, the composition of which is as follows.
| | |
|---|---|
| Sodium citrate ($Na_3O_6H_5O_7 \cdot 2H_2O$) | 1.26 g. |
| Citric acid ($H_3O_6H_5O_7 \cdot H_2O$) | 4.0 g. |
| Dextrose (anhydrous) | 11.0 g. |
| Distilled water to make 500 ml. | pH 6.0 |

*[3]DGV stands for Dextrose-Gelatin-Veronal, the composition of which is as follows
| | |
|---|---|
| 5 x Veronal buffer | 200 ml. |
| $CaCl_2$ (anhydrate) | 0.02 g. |
| $MgSO_4 \cdot 7H_2O$ | 0.12 g. |
| Gelatin | 0.6 g. |
| Dextrose (anhydrous) | 10 g. |
| Distilled water to make 1,000 ml. | pH 7.3 |

*[4]PBS has the following composition.
| | |
|---|---|
| NaCl | 8.0 g. |
| KCl | 0.2 g. |
| $KH_2PO_4$ | 0.2 g. |
| $Na_2HPO_4 \cdot 2H_2O$ | 14.4 g. |
| Distilled water to make 1,000 ml. | pH 7.2 |

---

Then, 0.25 volume of a 1:1 (volume/volume) mixture of formalin (The Pharmacopeia of Japan Eighth Edition) and -PBS of 2 times concentration was gradually added to the above red cell suspension under shaking, and the mixture was stored in a sealed container at 4° C. for 7 days.

The supernatant was removed by decantation. To the red blood cells thus fixed was added about 20 volumes of sterile distilled water, the resultant re-suspension was centrifuged at 1,500 r.p.m. for 5 minutes and the supernatant was discarded. This washing of fixed red blood cells was repeated 10 times to remove the salts from the cells. The fixed erythrocytes thus obtained are herein referred to briefly as SCRBC.

(3) Preparation of the pretreating composition

Using the above kaolin and SCRBC, the pretreating compositions given in Tables 1 to 4 were prepared. The conditions of lyophilization were as described below.

Vials of 25 ml. capacity were each filled with 10 ml. of a homogeneous suspension of 14% kaolin and 2% SCRBC in distilled water and, then, subjected to a rapid preliminary freezing treatment after shaking to re-establish the homogeneously suspended condition. Thereafter, the vials were applied with rubber stoppers for lyophilization and placed on the chamber rack of a freeze-dryer which had been cooled to $-40°$ C. to $-50°$ C. The vacuum lyophilization was carried out for 24 hours, after which the vials are purged with nitrogen gas and automatically sealed.

(4) 0.7 ml. of the above pretreating composition was admixed with 0.1 ml. of one of test sera for rubella virus HI, Japanese B encephalitis virus HI, Sendai virus (HVJ) HI and influenza virus HI reactions, each mixture was allowed to stand at room temperature for 30 minutes, with three shakings during the time, and then centrifuged at 2,000 r.p.m. for 20 minutes. The supernatant was then immediately subjected to the corresponding HI reaction to assay the HI antibody titer of the test serum. The HI tests were respectively performed in conformity with the procedures described in the following literature.

Rubella virus HI reaction: "Journal of Clinical Microbiology" 4, 188–189(1976);

Japanese B encephalitis virus HI reaction: "Microtiter Handbook" (1972), 404–411, Dynatech Corporation, Cambridge, Mass. (U.S.A.)

Sendai virus HI reaction: "Journal of Clinical Microbiology" 3, 91–95(1976); and Influenza virus HI reaction: "Journal of Clinical Microbiology" 4., 188–189(1976)

The results for rubella virus HI test are given in Table 1, the results for Japanese B encephalitis virus are given in Table 2; those for Sendai virus are shown in Table 3 and those for influenza virus are shown in Table 4.

TABLE 1

| | Pretreating composition | | | | | | | |
|---|---|---|---|---|---|---|---|---|
| | Suspension of 14% kaolin and 2% SCRBC (in) | | 1/10 volume of -PBS or BS 9.0 (10 times conc.) was added to a suspension of 14% kaolin and 2% SCRBC in distilled water | | A suspension of 14% kaolin and 2% SCRBC in distilled water was lyophilized and resuspended to original volume (in) | | Control Fresh erythrocytes of one-day chicks (-PBS) | |
| Human Serum No. | -PBS | BS 9.0 | -PBS | BS 9.0 | -PBS | BS 9.0 | Prior art 2-step method | Untreated serum |
| 1 | <8 | <8 | <8 | <8 | <8 | <8 | <8 | 128 |
| 2 | <8 | <8 | <8 | <8 | <8 | <8 | <8 | 256 |
| 3 | <8 | <8 | <8 | <8 | <8 | <8 | <8 | 256 |
| 4 | <8 | <8 | <8 | <8 | <8 | <8 | <8 | 256 |
| 5 | 16 | 16 | 16 | 16 | 16 | 16 | 16 | 256 |
| 6 | 32 | 32 | 32 | 32 | 32 | 32 | 32 | 256 |
| 7 | 32 | 64 | 32 | 64 | 32 | 64 | 32 | 256 |
| 8 | 64 | 64 | 64 | 64 | 64 | 64 | 64 | 256 |
| 9 | 64 | 128 | 64 | 128 | 64 | 128 | 64 | 256 |
| 10 | 256 | 256 | 256 | 256 | 256 | 256 | 256 | 256 |
| 11 | 256 | 512 | 256 | 512 | 256 | 512 | 256 | 256 |

TABLE 1-continued

| | Pretreating composition | | | | | | | |
|---|---|---|---|---|---|---|---|---|
| | Suspension of 14% kaolin and 2% SCRBC (in) | | 1/10 volume of -PBS or BS 9.0 (10 times conc.) was added to a suspension of 14% kaolin and 2% SCRBC in distilled water | | A suspension of 14% kaolin and 2% SCRBC in distilled water was lyophilized and resuspended to original volume (in) | | Control Fresh erythrocytes of one-day chicks (-PBS) | |
| Human Serum No. | -PBS | BS 9.0 | -PBS | BS 9.0 | -PBS | BS 9.0 | Prior art 2-step method | Untreated serum |
| 12 | 512 | 1024 | 512 | 1024 | 512 | 1024 | 512 | 512 |

TABLE 2

| | Pretreating composition | | | | | | | |
|---|---|---|---|---|---|---|---|---|
| | Suspension of 14% kaolin and 2% SCRBC (in) | | 1/10 volume of -PBS or BS 9.0 (10 times conc.) was added to a suspension of 14% kaolin and 2% SCRBC in distilled water | | A suspension of 14% kaolin and 2% SCRBC in distilled water was lyophilized and resuspended to original volume (in) | | Control (BS 9.0) | |
| Human Serum No. | -PBS | BS 9.0 | -PBS | BS 9.0 | -PBS | BS 9.0 | Prior art 2-step method | Untreated serum |
| 1 | <8 | <8 | <8 | <8 | <8 | <8 | <8 | 64 |
| 2 | <8 | 8 | <8 | 8 | <8 | 8 | 8 | 64 |
| 3 | 8 | 8 | 8 | 8 | 8 | 8 | 8 | 128 |
| 4 | 16 | 16 | 16 | 16 | 16 | 16 | 16 | 32 |
| 5 | 16 | 32 | 16 | 32 | 16 | 32 | 32 | 128 |
| 6 | 32 | 64 | 32 | 64 | 32 | 64 | 64 | 64 |
| 7 | 32 | 64 | 32 | 64 | 32 | 64 | 64 | 128 |
| 8 | 128 | 256 | 128 | 256 | 128 | 256 | 256 | 256 |

TABLE 3

| | Pretreating composition | | | | | | | |
|---|---|---|---|---|---|---|---|---|
| | Suspension of 14% kaolin and 2% SCRBC (in) | | 1/10 volume of -PBS or BS 9.0 (10 times conc.) was added to a suspension of 14% kaolin and 2% SCRBC in distilled water | | A suspension of 14% kaolin and 2% SCRBC in distilled water is lyophilized and resuspended to original volume (in) | | Control Fresh one-day-old chick erythrocytes and -PBS | |
| Mouse Serum No. | -PBS | BS 9.0 | -PBS | BS 9.0 | -PBS | BS 9.0 | Prior art 2-step method | Untreated serum |
| 1 | <8 | <8 | <8 | <8 | <8 | <8 | <8 | 32 |
| 2 | <8 | <8 | <8 | <8 | <8 | <8 | <8 | 32 |
| 3 | 8 | 8 | 8 | 8 | 8 | 8 | 8 | 64 |
| 4 | 32 | 32 | 32 | 32 | 32 | 32 | 32 | 32 |
| 5 | 64 | 64 | 64 | 64 | 64 | 64 | 64 | 64 |
| 6 | 64 | 64 | 64 | 64 | 64 | 64 | 64 | 64 |
| 7 | 256 | 256 | 256 | 256 | 256 | 256 | 256 | 256 |

TABLE 4

| Influenza virus Type | Test ferret serum | Serum No. | Pretreatment of test serum | | |
|---|---|---|---|---|---|
| | | | kaolin 14% SCRBC 2% in-PBS | 2-step method | Untreated control |
| A Kumamoto/22/76 | Immune serum | 1 | 128 | 128 | 256 |
| | | 2 | 256 | 256 | 256 |
| | | 3 | 256 | 256 | 256 |
| | Preimmune serum | 4 | <8 | <8 | 256 |
| | | 5 | <8 | <8 | 128 |
| | | 6 | <8 | <8 | 256 |
| B Gifu/2/73 | Immune serum | 7 | 128 | 128 | 128 |
| | | 8 | 128 | 128 | 256 |
| | | 9 | 128 | 128 | 256 |
| | Preimmune serum | 10 | <8 | <8 | 256 |
| | | 11 | <8 | <8 | 256 |
| | | 12 | <8 | <8 | 128 |

EXAMPLE 2

(1) Preparation of -PBS with added bovine serum albumin and gelatin $KH_2PO_4$ and $Na_2HPO_4$ were respectively dissolved in distilled water to prepare 1 M solutions and each solution was diluted to M/15 with 0.85% NaCl containing 0.4% bovine serum albumin and 0.005% of gelatin.

The two solutions were combined in a ratio to give a predetermined pH value.

(2) The HI reactions of Japanese B encephalitis virus a. Pretreatment of test sera Test human sera were pretreated either by the two-step method which comprised absorbing each serum with kaolin and, then, with SCRBC, or by the one-step method which comprised pretreating the serum with a mixture of kaolin and SCRBC according to this invention. In the case of the two-step method, (1) 0.3 ml. of -PBS (pH 7.2) was added to 0.1 ml. of the serum; (2) 0.4 ml. of a 25% suspension of kaolin in -PBS (pH 7.2) was added and, after intense stirring, the mixture was allowed to stand at room temperature for 20 minutes, with 2 to 3 shakings in the meantime; (3) the mixture was centrifuged at 2000 r.p.m. for 20 minutes, at the end of which time 0.1 ml. of a 10% suspension of SCRBC was gently added so as not to disturb the sediment, followed by gentle stirring; (4) the mixture was allowed to stand at 4° C. for 60 minutes, after which it was centrifuged at 2000 r.p.m. for 20 minutes. The supernatant (8-fold diluted serum) thus obtained was used in the HI test. In the case of the one-step method, 0.7 ml. of a mixture of 2% SCRBC and 14% kaolin as suspended in -PBS (pH 7.2) was added to 0.1 ml. of test serum and the mixture was stirred vigorously, then allowed to stand at room temperature for 30 minutes and finally centrifuged at 2000 r.p.m. The supernatant (8-fold diluted serum) thus obtained was used in the HI test.

b. Titration of HI antibodies

The determination of Japanese B encephalitis virus-HI antibody titers was carried out using permanent V microplates, by the standardized viral hemagglutination-inhibition procedure described in "Microtiter Handbook", referred to above, at pages 404–411, but with omitting the preliminary test.

As the reaction diluent, there was employed-PBS with added bovine serum albumin and gelatin in the pH range of pH 6.6 to 9.0, and the pretreated test serum, 4 hemagglutinating units of Japanese B encephalitis virus-specific HA antigen and SCRBC were diluted with the common buffer, mentioned above, of the same pH. 0.05 ml. of the pretreated serum (8-fold dilution) was put in the first well in the front row of the microplate and a doubling dilution series were prepared with 0.025 ml. each of the above diluent. Then, 0.025 ml. each of 4 hemagglutinating units of the HA antigen was added dropwise. On a micromixer, the diluted serum and HA antigen were thoroughly admixed. After 60 minutes standing at room temperature, 0.05 ml. each of a 0.4% suspension of SCRBC was added dropwise. The system was thoroughly shaken again on a micromixer and incubated at 37° C. for 60 minutes. The HI readings were taken to determine the HI antibody titers of the test sera for Japanese B encephalitis virus.

The results are set forth in Table 5.

TABLE 5

(Japanese B encephalitis virus-HI antibody titer)

| Pretreatment of test serum pH of the diluent | Two-step method | | | | One-step method | | | |
|---|---|---|---|---|---|---|---|---|
| | 6.6 | 7.2 | 8.0 | 9.0 | 6.6 | 7.2 | 8.0 | 9.0 |
| Human serum | | | | | | | | |
| No.1 | 512 | 512 | 512 | 512 | 512 | 512 | 512 | 512 |
| No.2 | 128 | 128 | 128 | 128 | 128 | 128 | 128 | 128 |
| No.3 | 128 | 128 | 128 | 128 | 128 | 128 | 128 | 128 |
| No.4 | 32 | 32 | 32 | 32 | 32 | 32 | 32 | 32 |
| No.5 | <8 | <8 | <8 | <8 | <8 | <8 | <8 | <8 |

Industrial Applicability

According to the present invention, both the non-specific hemagglutination inhibitors and the natural hemagglutinins in a test serum for a virus HI reaction can be removed at one stroke without giving adverse affect on the activity of a virus-specific HI antibody occurring in the same serum, by pretreating the test serum with a composition containing both fixed avian erythrocytes and kaolin particles. By subjecting the thus-pretreated test serum to a virus HI reaction, the virus HI antibody titer of the test serum can be determined with accuracy and high sensitivity for serological diagnosis.

I claim:

1. In an arbovirus hemagglutination-inhibition test reaction which comprises pretreating a test serum for an arbovirus hemagglutination-inhibitors, mixing the pretreated test serum with an arbovirus-specific hemagglutinating antigen and then adding erythrocytes to assess occurrence of hemagglutination, the improvement which comprises (1) pretreating the test serum with a composition containing both fixed avian erythrocytes and kaolin particles, (2) employing the fixed avian erythrocytes as the erythrocytes to be agglutinated, and (3) diluting, respectively, the pretreated test serum, the arbovirus-specific hemagglutinating antigen and the fixed avian erythrocytes with a single common buffer in the pH range of 6.6 to 12.0.

2. A method as claimed in claim 1, wherein the pretreatment is conducted by contacting the test serum with the said composition in an aqueous medium for a time sufficient to remove the non-specific hemagglutination-inhibitors and natural hemagglutinins occurring in the test serum.

3. A method as claimed in claim 1, wherein the fixed avian erythrocytes are of chick origin.

* * * * *